United States Patent [19]

Wesley

[11] Patent Number: 4,470,204
[45] Date of Patent: Sep. 11, 1984

[54] CONTROL DEVICE FOR A LAUNDRY DRIER

[75] Inventor: Victor J. Wesley, London, England

[73] Assignee: U.S. Philips Corporation, New York, N.Y.

[21] Appl. No.: 399,930

[22] Filed: Jul. 19, 1982

[30] Foreign Application Priority Data

Jul. 22, 1981 [GB] United Kingdom ............... 8122582

[51] Int. Cl.³ ............................................. F26B 19/00
[52] U.S. Cl. ............................................. 34/48; 34/53; 34/55
[58] Field of Search ....................... 34/48, 53, 55, 133; 361/178, 212

[56] References Cited

U.S. PATENT DOCUMENTS

| | | | |
|---|---|---|---|
| 3,491,458 | 1/1970 | Elders et al. ........................ | 34/55 |
| 4,215,486 | 8/1980 | Heyer et al. ........................ | 34/53 |
| 4,385,451 | 5/1983 | Wesley ................................ | 34/133 |

FOREIGN PATENT DOCUMENTS 116769  9/1979  Japan ...................................... 34/55

Primary Examiner—Larry I. Schwartz
Assistant Examiner—David Westphal
Attorney, Agent, or Firm—Robert T. Mayer; Bernard Franzblau

[57] ABSTRACT

A control device for a laundry drier of the kind in which mechanical movement of the laundry load in a drum causes the article(s) constituting the load to form an electrically resistive connection between contact electrodes 5 and 6 in the drum. An a.c. sensing current is fed from a transformer T1 via the load and through a series capacitor C2 such that the voltage across the capacitor C3 is an inverse function of the state of dryness of the articles. This voltage is compared in a comparator TR1 with a reference voltage Vref which is chosen so that the comparator TR1 produces an output signal when the articles of the load have reached a predetermined dryness. Any electrostatic charges developed in the load are suppressed by a unidirectional low impedance shunt comprising a diode D8 and a resistor R12 in series.

9 Claims, 2 Drawing Figures

CONTROL DEVICE FOR A LAUNDRY DRIER

This invention relates to a control device for a laundry drier of the kind in which mechanical movement of the laundry load in a drum causes the article(s) constituting the load to form, at least intermittently, an electrically resistive connection between contact electrodes accessible to the load, the resistance of which connection is representative of the state of dryness of the load. The device includes means for causing an alternating sensing current to flow through a circuit element and, via said electrodes, through said resistive connection such that a voltage is developed across said circuit element which depends upon the value of the said resistance, and a comparator for comparing the said voltage with a reference potential.

Such a control device is described in U.S. Pat. No. 4,385,451, in which the circuit element is a resistor and the reference potential is selected in relation to the value of the resistor such that the comparator gives an output signal when a given state of dryness of the load has been reached. The resistance of the resistor may be variable in order to vary the degree of dryness obtained and the resistor is referred to hereinafter as a scaling resistor.

If the drum of the laundry drier does not contain a load, then the resistance between the electrodes should have such a high value (theoretically infinity) that it represents a completely dry load. Thus if the drier were switched on without a laundry load, the resultant output signal from the comparator would, depending upon the particular type of drier, generally either switch the drier off or switch off an air heater. It has been found that the spreads in production tolerances can create a situation in which the comparator does not always give an output signal in these circumstances.

This has been found to be due to the inherent stray capacitance of the drum and electrode slip rings as seen between the two electrodes. This capacitance varies according to the mechanical arrangement of the machine concerned, but is typically of the order of 500 to 1500 pF. With an AC supply frequency of 50 Hz, the impedance of a 500 pF capacitor is 6.37 Mohm. With a scaling resistor having a typical value of 2.2 Mohm, the voltage across the latter is close to the "dry" indication voltage that would cause the comparator to give its output signal. This is in part due to the fact that the voltage (Vc) across the reactance of the capacitor is 90° out of phase with the voltage (Vr) across the scaling resistor—in other words Vr is much higher than it would be if the capacitor were a resistor having the same impedance and the two voltages were in phase.

Further, this capacitive impedance is in parallel with the resistance of the articles of the load when the drier is in normal use. This has little effect while the articles are still moist and produce a relatively low resistance between the electrodes, but it has a significant effect on the combined impedance when the load is approaching the acceptably dry state. The problem here is that the capacitance may vary quite considerably (e.g. ±15%) from drier to drier and, therefore, these differing capacities cause the comparators concerned to respond to different states of dryness. Hence the dryness levels produced can vary very widely from drier to drier.

An object of the invention is to mitigate these disadvantages.

A further problem in laundry driers is that the mechanical movement of the articles of the load causes electrostatic charges to be produced when the articles (fabrics) are in the partially dry state. Although an attempt has been made to use these charges as an indication of the state of dryness of the load (see, for example, U.K. patent specification No. 1,464,664), attempts are usually made to suppress such charges. Where moisture-sensing control devices are used, the electrostatic charges can adversely affect the sensing operation. Thus, for example, U.S. Pat. No. 3,729,833 discloses a control device which includes a capacitor which is charged via a diode from a direct current power supply and the capacitor is coupled to the drum electrodes by a series resistor-capacitor combination. The specification states that the capacitor supplies neutralising current when a negative electrostatic charge appears across the electrodes and it absorbs current when a positive electrostatic charge appears across the electrodes. Thus use is made of decoupling capacitors to bypass the (high frequency) static signals, thus allowing the sensing system to be properly monitored by the sensing circuit. A similar system is disclosed in U.S. Pat. No. 3,758,959 which uses a blocking diode and a filter capacitor. These systems, however, use d.c. sensing and are not suitable for use with control devices using alternating current sensing. A further object of the invention is to mitigate the effects of electrostatic charges in an a.c. sensing type of control device.

According to the invention, there is provided a control device of the type defined in the opening paragraph, characterised in that the said circuit element is a capacitor and in that the device further includes means for connecting a resistor and a diode in series across said electrodes.

The use of a scaling capacitor instead of the prior art scaling resistor means that the a.c. voltages across the electrodes and across the scaling capacitor are substantially in phase with each other and, therefore, the voltage across the scaling capacitor is considerably less than that which would be produced across a scaling resistor having a resistance which is equal to the reactance of the capacitor. Therefore the problems referred to above in relation to the "no laundry load" condition are mitigated to such an extent that quite wide variations in capacitance between the electrodes can be accommodated without the control device failing to respond under the said condition. Also, the variation in sensing levels between similar driers is substantially reduced.

A high value resistor (e.g. 10 Mohm) may be connected in parallel with the scaling capacitor, if required, to ensure that the latter does not acquire a permanent charge.

We have found that electrostatic charges cause problems when using a scaling capacitor and that these problems are at least mitigated by connecting a shunting circuit across the electrodes which, due to the diode, offers a relatively high impedance to electrostatic charges of one polarity across the electrodes and a relatively low quenching impedance to charges of the opposite polarity.

An embodiment of a control device in accordance with the invention will now be described by way of example with reference to the accompanying drawings, in which.

Figure 1:
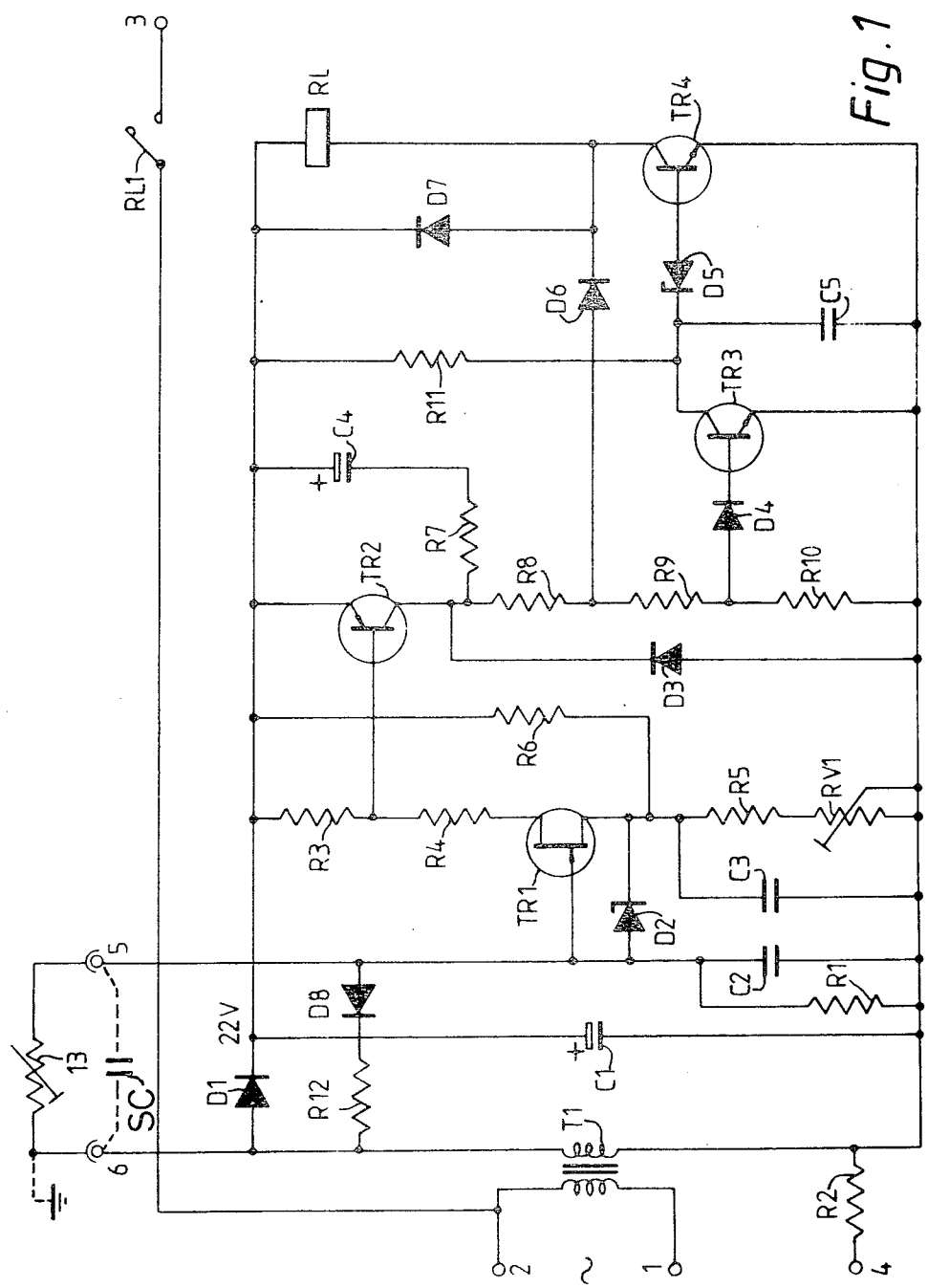
FIG. 1 shows a circuit diagram of the invention.

In FIG. 1, the electrical resistance of the articles comprising the load is represented by a moisture-sensitive resistor 13 connected between electrodes 5 and 6 mounted on a rotatable drum, electrical connection to the electrodes being made via slip rings or other means such as door electrodes. The inherent capacitance of the mechanical arrangement including the slip-rings is represented by a stray capacitance SC connected by broken lines to the two electrodes.

The circuit is powered from an a.c. mains power supply which is applied to terminals 1 and 2. The primary of a transformer T1 is connected to these terminals and terminal 2 is connected, via the contact RL1 of an electromechanical relay RL, to an output terminal 3 of the device. Transformer T1 steps down the ac mains potential to the required voltage and also provides electrical isolation from the power supply which can allow the secondary circuit to be grounded, if necessary (shown in broken line).

A diode D1 rectifies the secondary voltage and capacitor C1 smooths the D.C. potential required to power the circuit, the value of capacitor C1 being large enough to give adequate smoothing of mains ripple during operation, but small enough to discharge and hence allow the circuit to reset within a few seconds following mains switch-off. In the drier, the electrode 6 forms one sensing probe while electrode 5, the other sensing probe, is connected in series with a capacitor C2 in order to form a potential divider with the resistance 13 of the damp fabrics of the load. A discharge resistor R1 is connected in parallel with capacitor C2. The midpoint of the divider (electrode 5) is connected to the gate terminal of a field effect transistor TR1. In this embodiment, the use of a junction gate field effect transistor, preferably an N-channel-junction FET, was selected because its very high gate impedance is unlikely to influence the potential at the divider midpoint whereas the base current of a normal bi-polar device might. Resistor R2 is provided so that a switch (not shown) between terminals 4 and 5 may connect it in parallel with resistor R1 and capacitor C2 to allow the drying to be terminated at a different load resistance. Transistor TR1 is used in this circuit in order to compare the peak potential across the wash load with a set reference potential Vref at its source terminal. This potential Vref is established by the potential dividing action of resistor R6 with resistors R5 and RV1, the transistor being decoupled by capacitor C3. The prior adjustment of resistor RV1 takes account of circuit variables such as gatesource characteristics and resistor tolerances. Zener diode D2 provides protection for transistor TR1 against any excessive negative voltage excursion at its gate terminal.

A positive peak potential greater than the reference potential will cause transistor TR1 to conduct, thus drawing base current from transistor TR2 via resistor R4 and causing transistor TR2 also to conduct (resistor R3 acts to guard against the possibility of undesired leakage paths causing transistor TR2 to conduct). The conduction of transistor TR2 causes timing capacitor C4 (previously charged as described below) to discharge rapidly via resistor R7, thus resetting the sampling period.

The sampling period is achieved by capacitor C4 charging via resistors R7, R8 and R9 into the base electrode of transistor TR3 via diode D4. Thus so long as the capacitor C4 charging current is sufficient to keep transistor TR3 conducting, transistor TR4 will be starved of base current since zener diode D5 is prevented from conducting. As capacitor C4 charges, the current through resistors R7, R8 and R9 will decrease with an exponential decay until the current into the base electrode of transistor TR3 is no longer sufficient to keep transistor TR3 in conduction and its collector electrode voltage will rise due to the presence of resistor R11. When the voltage at the transistor TR3 collector electrode is greater than the zener voltage of diode D5 (e.g. 13 volts), base current will flow into transistor TR4 causing it to conduct and, in turn, to energise the coil of relay RL causing the associated relay contacts RL1 to close and connect terminal 3 to mains supply terminal 2.

Latching action of the circuit is provided by feedback from transistor TR4 via diode D6 to the junction of resistors R8 and R9 such that when transistor TR4 is conducting the voltage difference between the junction of resistors R8 and R9 and zero volts is never greater than the inherent saturation voltage of transistor TR4 plus the forward voltage drop of diode D6. This, when divided by the action of resistors R9 and R10 and further "dropped" by diode D4, ensures that transistors TR3 is held out of conduction.

In addition to providing for the actual functioning of the circuit, certain other requirements have been considered. For example it is necessary that, after the circuit has sensed a dry wash load and has then been switched off by the operator, then within a few seconds the circuit will re-establish its quiescent "sensing state" once power is re-applied. To this end (as already mentioned) the value of capacitor C1 is made as low as possible and diode D3 is included in order to discharge capacitor C4 quickly after switchoff.

To ensure that the circuit can establish itself in the correct state at "switch-on", zener diode D5 is dimensioned in order to allow transistor TR3 to turn-on before transistor TR4.

Figure 2:
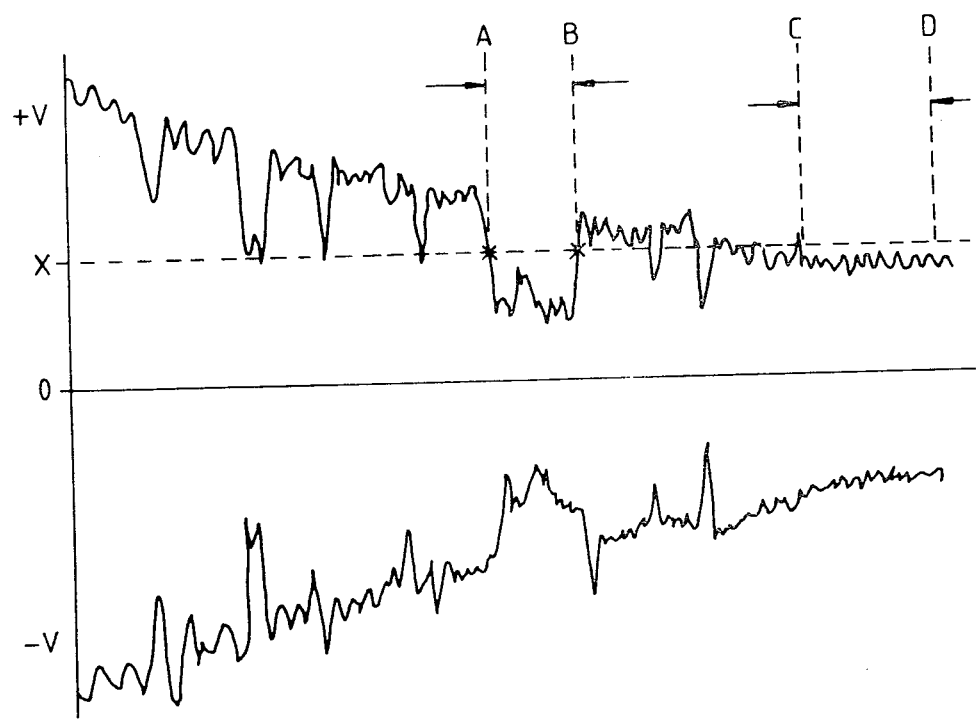
FIG. 2 is a graph of waveforms in the circuit during operation.

FIG. 2 shows on a vertical axis the "envelope" of the peak A.C. voltage waveform V that may appear across the scaling capacitor C2 towards the end of a drying operation.

At instant A the voltage falls below the preset reference potential value X, and remains low until instant B, say 40 seconds later. This period is less than the chosen sampling period (say 45 seconds) and capacitor C4 is discharged, thus resetting the timing circuit. The drying operation is allowed to continue until instant C, where once again the level falls below the reference potential, but now remains low for longer than 45 seconds and at instant D, the end of the 45 seconds timing period, the drying process is terminated.

In summary, the capacitor C2, together with resistor R1 and whatever resistance value appears when the contact terminals in the drum are bridged across by the load, acts as a first potential divider and a voltage proportional to the electrical resistance of the washing articles is applied to the gate electrode of the field effect transistor TR1. A rise of potential across the plates of capacitor C4 causes operation of an output switch comprising transistors TR3, TR4 and relay RL. Transistors TR3 and TR4 are connected together in a manner somewhat analogous to that of a Schmitt trigger circuit so that a potential above a predetermined level on the base electrode of transistor TR3 will cause the connection between the emitter and collector electrodes of transistor TR4 to become conductive and the relay RL will be energised. When the voltage on the base of transistor TR3 is below the predetermined level, the relay RL will not be energised.

When the capacitor C4 is allowed to become fully charged, the base electrode of transistor TR3 becomes starved of base current and transistor TR4 is turned on. The relay RL is thus energised and an associated relay contact R1 is moved to a MAKE condition causing output terminal 3 to be brought to the mains potential.

The value of C2 is chosen in dependence upon the values of the stray capacitance SC and of Vref, and will vary widely from manufacturer to manufacturer. In order to provide optimum effect the capacitance of capacitor C2 is preferably arranged to be between two and five times the stray capacitance that exists between electrodes 5 and 6. In a particular embodiment, the value of SC was 460 pF, the value of C2 was 1500 pF, and Vref was 8.5 Volts. The function of R1 is to prevent a charge from building up on capacitor C2 under idle conditions and possibly switching transistor TR1 on. The resistance of resistor R1 is made fairly high relative to the reactance of capacitor C2; for example 10 Mohm.

Diode D8 and resistor R12 serve to suppress any electrostatic charges appearing across electrodes 5 and 6. We have discovered that the electrostatic discharges are capacitive in nature with the fabrics of the load serving as the dielectric between "capacitor" electrodes 5 and 6. The charge on the dielectric will be presented at the electrodes with an arbitrary sense, due to the mechanical tumbling of the clothes during the drying operation, and will be shared with capacitor C2. With the control circuit connected across the electrodes as shown in FIG. 1, there will be no effect when the fabrics take on a negative charge with respect to ground as in this case a negative voltage transient with respect to −22 V will appear at its input and the circuit has been designed to respond only to positive peak voltages. When the fabrics acquire a positive charge with respect to ground, then an instantaneous voltage equal to the shared charge voltage with capacitor C2 will be impressed across the electrodes causing a positive transient at the sense circuit input with respect to −22 V. The duration of the transient will depend upon its energy and upon the impedance presented for discharging the electrostatic charge.

Due to the charge on the fabrics accumulating with respect to ground and not the −22 V rail, the charge on the fabrics can be effectively discharged through a low impedance path across the electrodes directly to ground rather than through the scaling components, the −22 V rail, and then the power supply to ground, thus reducing the disturbance at the sense circuit imput. The low impedance path needs only to conduct when positive voltages w.r.t. ground appear across the drum and therefore comprises diode D8 and resistor R12.

The inclusion of diode D8 in the electrostatic "low impedance" discharge path effectively isolates the low impedance path from parallel connection across the laundry load on the positive excursion of the a.c. waveform across the drum. Thus the performance of the sensing circuit is not significantly altered.

The actual discharge path impedance (resistor R12=2.2 MΩ) was selected as being low enough to effectively shunt the electrostatic charge to ground while being high enough not to significantly distort the a.c. waveform across the electrodes. With this series diode/resistor combination the 2.2 MΩ resistor R12 only affects the sensing circuit waveform on the negative excursion of the a.c.

Under conditions where static is being generated in a tumble drier fitted with a.c. sensing, the viewed waveform across the drum electrodes as it appears on an oscilloscope can suffer instantaneous d.c. shifts due to static of more than 10 V on the nominal 24 V rms across the drum, and this can seriously affect the sensing performance. With the 2.2 MΩ and series diode included in the circuit this d.c. shift due to static is reduced to acceptable levels.

I claim:

1. A control device for a laundry drier of the kind in which mechanical movement of a laundry load in a drum causes articles constituting the laundry load to form, at least intermittently, an electrically resistive connection between contact electrodes accessible to the load, the resistance of said connection being indicative of the state of dryness of the load; the control device comprising: means for causing an alternating sensing current to flow through a capacitor and, via said electrodes, through said resistive connection such that a voltage is developed across said capacitor which depends upon the value of said resistance, and a comparator for comparing said voltage with a reference potential, and means for connecting a resistor and a diode in series across said electrodes.

2. A control device as claimed in claim 1, further comprising a resistor connected in parallel with the capacitor.

3. A control device as claimed in claim 1 wherein the contact electrodes exhibit a stray capacitance therebetween and said capacitor has a capacitance of between two and five times said stray capacitance between the contact electrodes.

4. A control device for a laundry dryer of the kind which includes a pair of contact electrodes wherein a mechanical movement of a laundry load causes at least some articles of said load to form, at least intermittently, an electrically resistive connection between said contact electrodes, the resistance of said connection being indicative of the state of dryness of the load, said control device comprising: a scaling capacitor, means for causing an alternating current to flow through said scaling capacitor and, via said contact electrodes, through said resistive connection so that a voltage is developed across said scaling capacitor which is determined by the resistance value of the resistive connection, a comparator for comparing said voltage with a reference voltage, a resettable timing circuit having a given operating time interval and coupled to an output of the comparator so as to be reset whenever a given relationship exists between said voltage and said reference voltage, an output switch operated by said timing circuit, and means coupling a resistor and a diode in series across the contact electrodes so as to suppress an electrostatic charge when developed by the laundry load.

5. A control device as claimed in claim 4 further comprising a resistor connected in parallel with the scaling capacitor, the resistance of said resistor being fairly high relative to the impedance of the scaling capacitor.

6. A control device as claimed in claim 5 wherein the contact electrodes exhibit a stray capacitance and said scaling capacitor has a capacitance between two and five times said stray capacitance.

7. A control device as claimed in claim 4 wherein the contact electrodes exhibit a stray capacitance and said scaling capacitor has a capacitance between two and five times said stray capacitance.

8. A control device as claimed in claim 4 wherein the timing circuit comprises a resistance-capacitance circuit including a capacitor coupled to a source of DC voltage and a semiconductor switch coupled to the capacitor to provide a discharge path therefor and responsive to the output of the comparator to discharge the capacitor whenever said contact electrodes contact a moist load article within said given time interval thereby to reset the timing circuit.

9. A control device as claimed in claim 4 wherein the scaling capacitor is connected to said contact electrodes so that the resistive connection and the scaling capacitor are in series so as to form a voltage divider across a pair of terminals for supplying said alternating current.

* * * * *

UNITED STATES PATENT AND TRADEMARK OFFICE
CERTIFICATE OF CORRECTION

PATENT NO.   : 4,470,204
DATED        : September 11, 1984
INVENTOR(S)  : VICTOR J. WESLEY It is certified that error appears in the above-identified patent and that said Letters Patent is hereby corrected as shown below:

Claim 1, line 15, after "electrodes" insert --to suppress an electrostatic charge when developed by the laundry load--

Signed and Sealed this

Eighth Day of October 1985

[SEAL]

Attest:

DONALD J. QUIGG

Attesting Officer

Commissioner of Patents and Trademarks—Designate